(12) United States Patent
Kersting

(10) Patent No.: US 8,903,145 B2
(45) Date of Patent: Dec. 2, 2014

(54) METHOD AND APPARATUS FOR IMAGE PROCESSING FOR COMPUTER-AIDED EYE SURGERY

(75) Inventor: Oliver Kersting, Berlin (DE)

(73) Assignee: Alcon Pharmaceuticals Ltd., Fribourg (CH)

( * ) Notice: Subject to any disclaimer, the term of this patent is extended or adjusted under 35 U.S.C. 154(b) by 894 days.

(21) Appl. No.: 13/125,682

(22) PCT Filed: Oct. 20, 2009

(86) PCT No.: PCT/EP2009/063753
§ 371 (c)(1),
(2), (4) Date: Jun. 10, 2011

(87) PCT Pub. No.: WO2010/046371
PCT Pub. Date: Apr. 29, 2010

(65) Prior Publication Data
US 2011/0230751 A1 Sep. 22, 2011

(30) Foreign Application Priority Data
Oct. 22, 2008 (EP) .................................. 08167232

(51) Int. Cl.
*G06K 9/00* (2006.01)
*G06T 7/00* (2006.01)
*A61F 9/007* (2006.01)
*A61B 3/00* (2006.01)
*A61F 9/008* (2006.01)
*A61F 2/16* (2006.01)

(52) U.S. Cl.
CPC ......... *A61F 9/00736* (2013.01); *G06T 7/0024* (2013.01); *G06T 2207/30041* (2013.01); *A61B 3/0025* (2013.01); *A61F 2009/00846* (2013.01); *G06T 2207/10016* (2013.01); *G06T 7/0016* (2013.01); *A61F 2/1662* (2013.01)
USPC ........... 382/128; 382/276; 382/294; 382/295; 606/4; 606/6; 351/206; 351/208; 351/209; 351/210

(58) Field of Classification Search
None
See application file for complete search history.

(56) References Cited

U.S. PATENT DOCUMENTS 7,040,759 B2 * 5/2006 Chernyak et al. ............. 351/246
7,044,602 B2 * 5/2006 Chernyak ...................... 351/208
(Continued)

FOREIGN PATENT DOCUMENTS

CN 1650148 8/2005
CN 101068515 11/2007
(Continued)

OTHER PUBLICATIONS

Fleming et al., "Intraoperative Visualization of Anatomical Targets in Retinal Surgery", Jan. 7-9, 2008, WACV 2008. IEEE Workshop on, vol. 1, No. 6, pp. 7-9.*

Primary Examiner — Matthew Bella
Assistant Examiner — Jason Heidemann
(74) Attorney, Agent, or Firm — Haynes and Boone, LLP

(57) ABSTRACT

Image processing for computer-aided eye-surgery includes acquiring a reference image of the eye and enriching said reference image by inserting additional context information which are helpful for a surgeon when performing the eye surgery. The reference image is registered with a real time image of the eye. The context information is overlayed over the real time image of the eye based on a tracking of the eye movement such that the context information is displayed at the same position despite a movement of the eye.

13 Claims, 10 Drawing Sheets

Diagnostic/Reference Image → Insert Context Information → Registration/Coordinate Transformation → Overlay

(56) References Cited

U.S. PATENT DOCUMENTS

| | | | |
|---|---|---|---|
| 7,899,226 | B2 | 3/2011 | Pescatore et al. |
| 8,556,885 | B2 * | 10/2013 | Hohla et al. .............. 606/5 |
| 2003/0223037 | A1 | 12/2003 | Chernyak |
| 2005/0025365 | A1 | 2/2005 | Oosawa |
| 2006/0247659 | A1 * | 11/2006 | Moeller et al. ............ 606/107 |
| 2008/0013809 | A1 * | 1/2008 | Zhu et al. ................. 382/128 |
| 2008/0312675 | A1 * | 12/2008 | Newcott et al. ........... 606/166 |
| 2010/0317962 | A1 * | 12/2010 | Jenkins et al. ............ 600/411 |
| 2011/0202046 | A1 * | 8/2011 | Angeley et al. ............ 606/6 |
| 2014/0126700 | A1 * | 5/2014 | Gertner et al. ............ 378/65 |

FOREIGN PATENT DOCUMENTS

| | | |
|---|---|---|
| DE | 102008017111 A1 | 10/2008 |
| JP | 2005528600 | 9/2005 |
| JP | 2006136714 | 6/2006 |
| JP | 2007175494 | 7/2007 |
| JP | 2008521508 | 6/2008 |
| JP | 4256342 | 4/2009 |
| JP | 4851468 | 1/2011 |
| JP | 5006020 | 8/2012 |
| JP | 5130424 | 1/2013 |
| WO | WO 2006060323 | 6/2006 |
| WO | WO2006/060323 A1 | 8/2006 |
| WO | WO 2008/008044 A2 | 1/2008 |

* cited by examiner

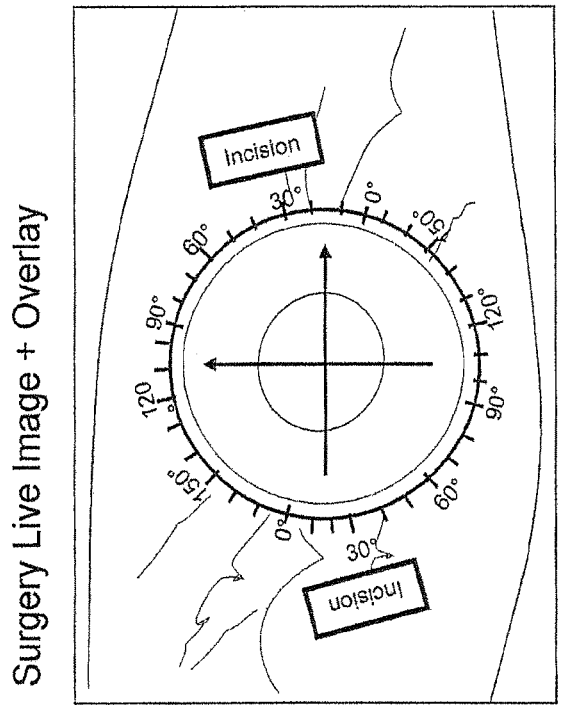
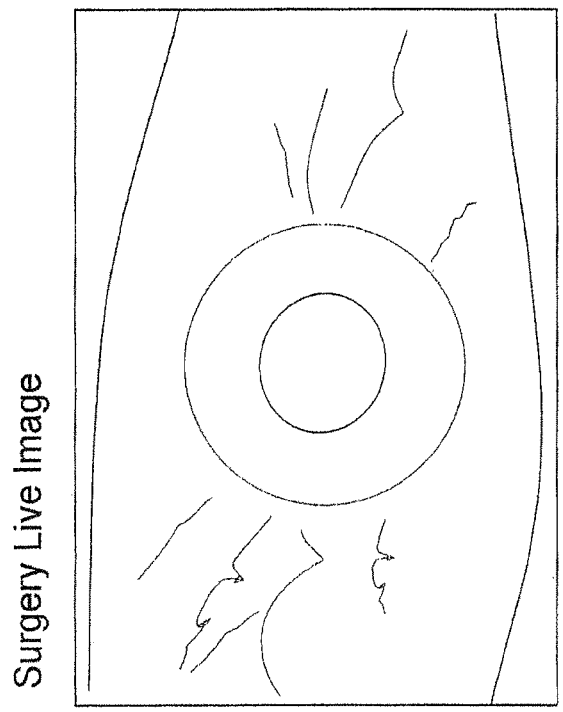
Fig. 4

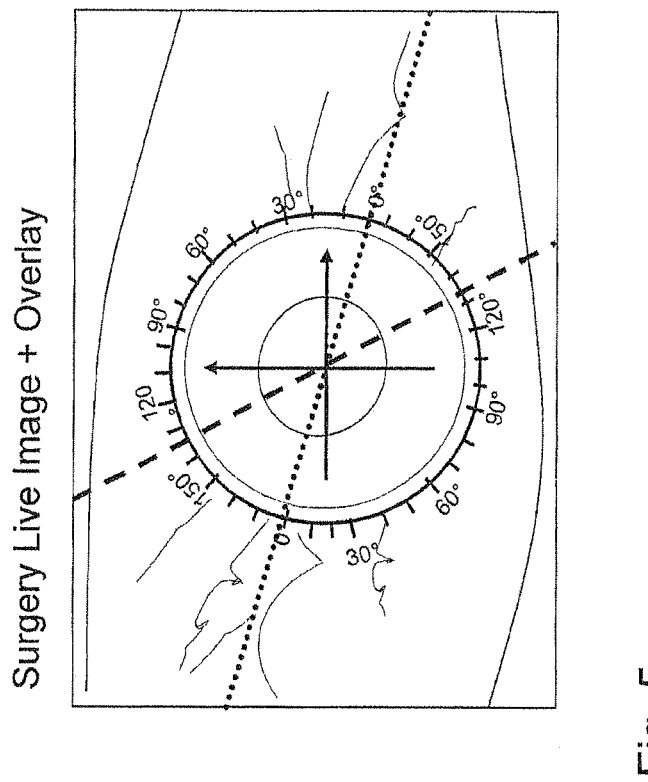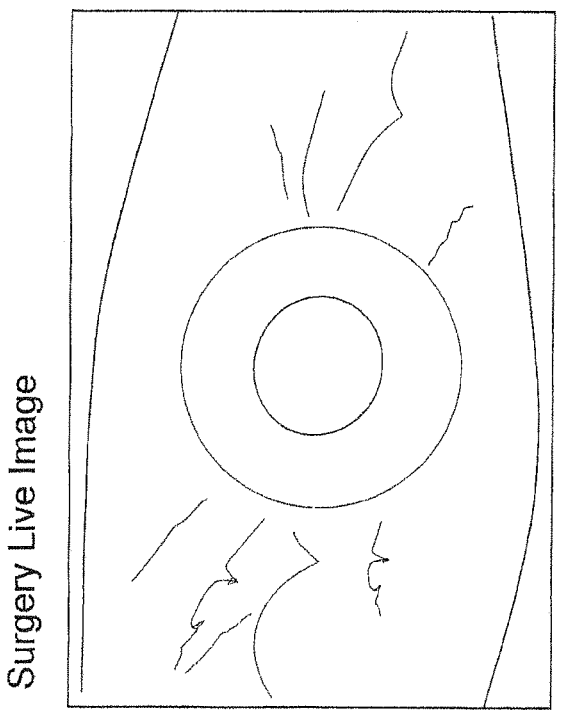
Fig. 5

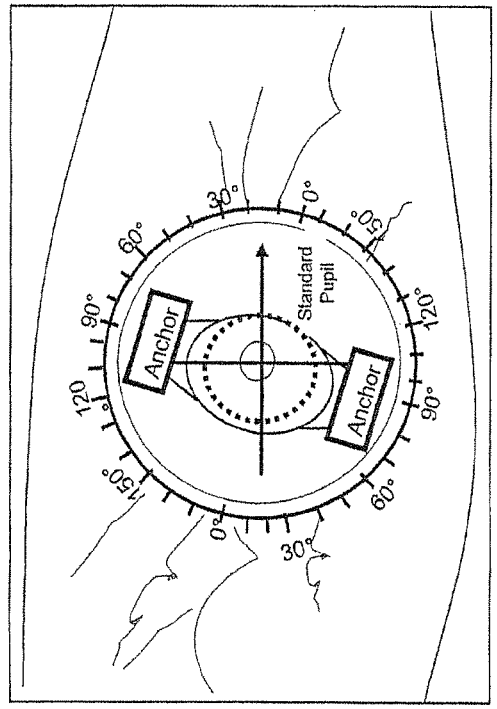
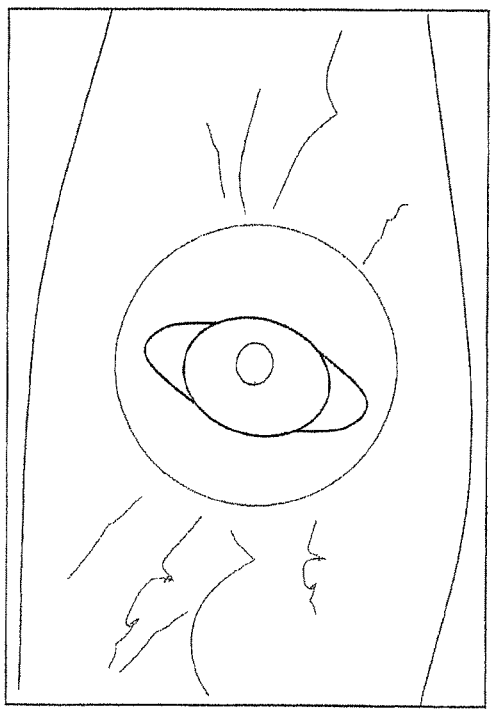
Fig. 6

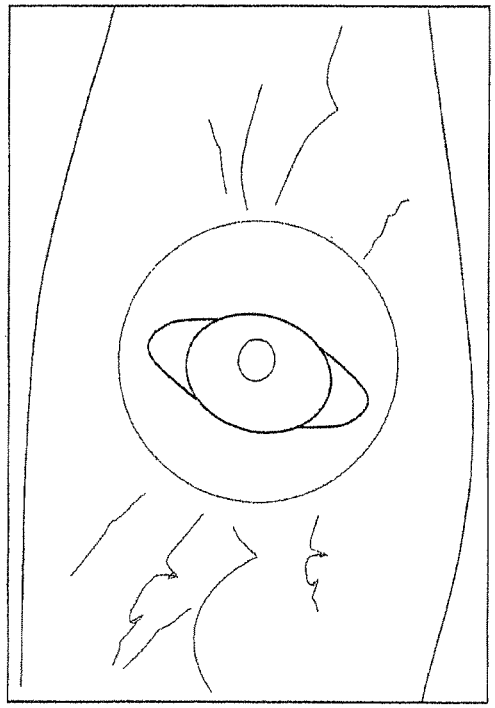
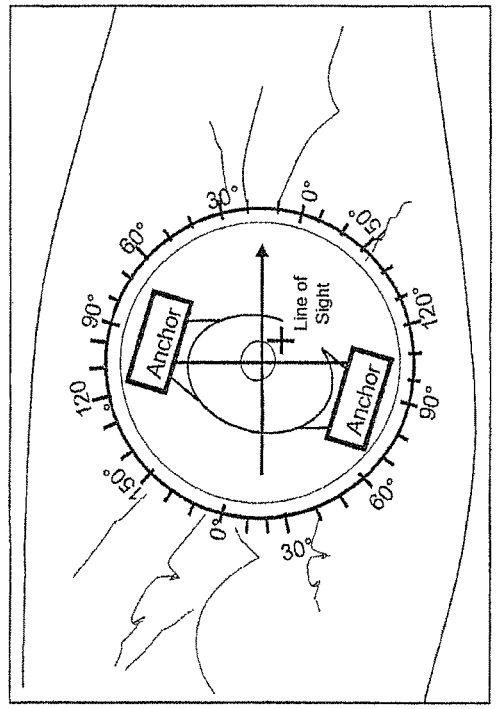
Fig. 7

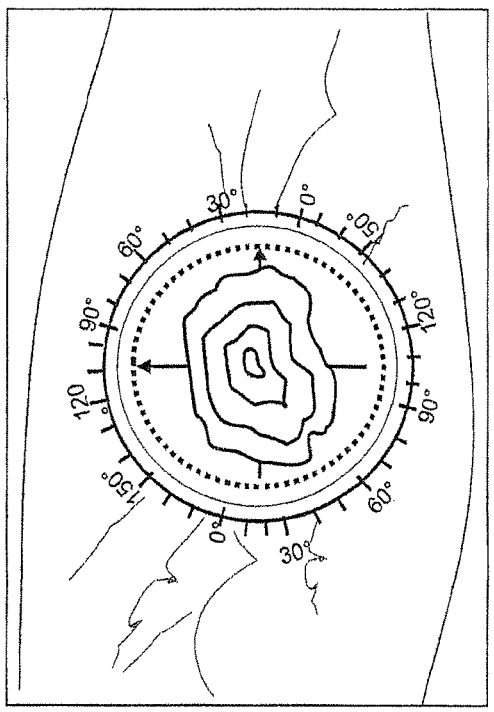
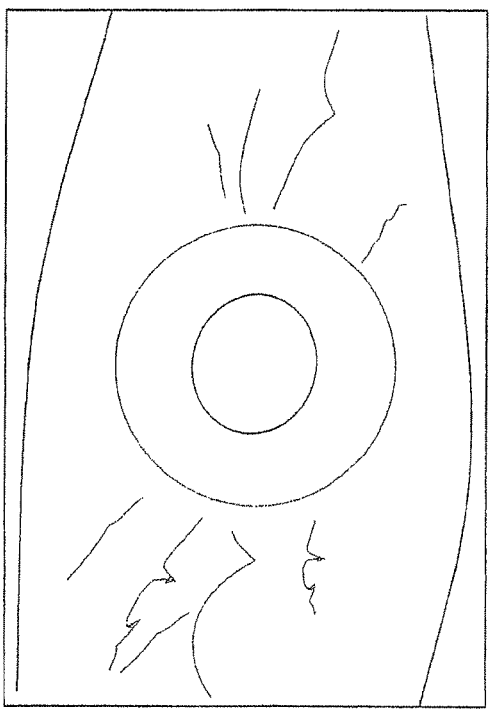
Fig. 8

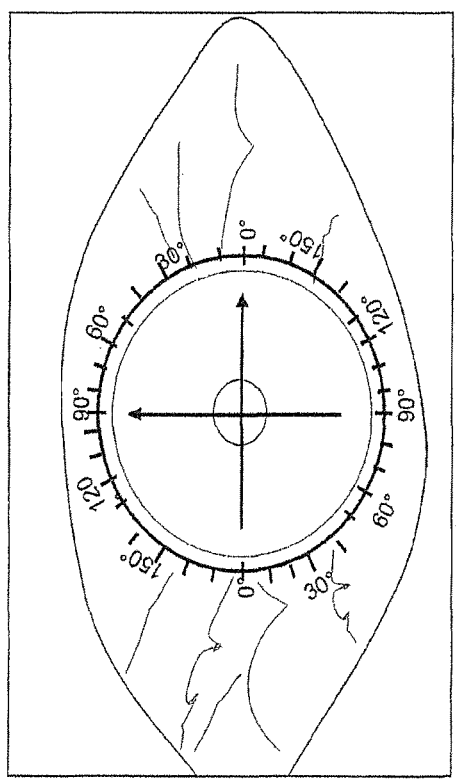
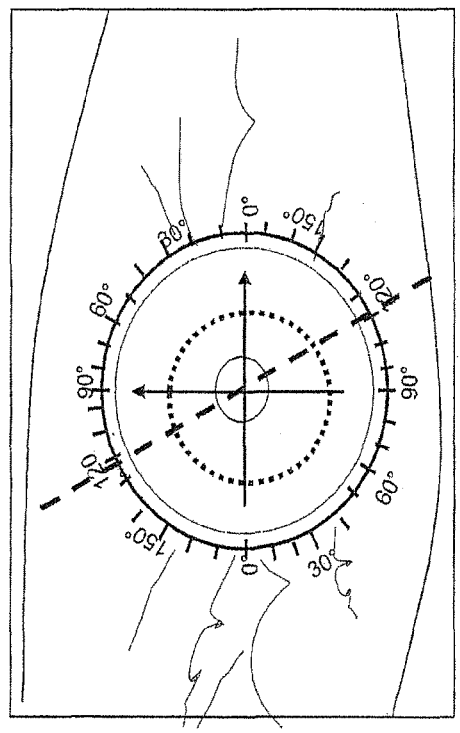
Fig. 10

METHOD AND APPARATUS FOR IMAGE PROCESSING FOR COMPUTER-AIDED EYE SURGERY

FIELD OF THE INVENTION

The present invention relates to a method and an apparatus for computer aided eye surgery, particularly for intraocular lens surgery planning using eye registration and tracking.

BACKGROUND OF THE INVENTION

In the prior art the process of intraocular lens (IOL) surgery is a cumbersome process for the surgeon. The classical process according to the prior art may involve four steps, namely i) diagnosis, ii) pre-surgery preparation, iii) surgery preparation, iv) lens removal and implantation, and finally v) surgery finalisation. The whole process is outlined in somewhat more detail in the following.

A first step involves the diagnosis of the eye to be treated. Usually the geometry of an eye (length, chamber depth, lens thickness, etc.) is determined using a device like an IOL Master from Zeiss. It may further include a topometry measurement to measure the corneal surface of the eye. Moreover, it may include the use of a refractometer to determine the visual performance of the eye. This diagnostic data is used to define the IOL type and IOL geometry that should be implanted.

A second step consists of the pre-surgery preparation. This means the preparatory work done by the surgeon to "plan" the surgery, such as "where to cut", etc. This may include e.g. the marking of the reference vertical and horizontal axes on the eye, typically by a pen. Moreover, it may involve the graphical marking of a hardcopy of a diagnostic image using a pen.

A third step consists of the surgery preparation. This involves e.g. anesthesia, desinfection and lid speculum in the eye. If the surgery involves a toric IOL, this also involves the marking of the astigmatism axis with marking pen or special axis marker (Mendez Ring) for later final IOL orientation. The third step further includes the preparation of incisions for instruments and for implanting the lens. Finally a viscoelastica is injected to the eye to ensure a smooth lens implantation.

A fourth step includes the actual surgical steps, such as capsulorhexis, hydrodissection, phacoemulsification, and of course then the lens implantation.

A fifth step of the whole procedure is the surgery finalisation, which may e.g. involve the alignment of the IOL, for toric IOLs the angular positioning of the IOL, and finally the removal of the viscoelastica.

The whole procedure is schematically illustrated in FIG. 1. It should be noted that these steps, especially the pre-surgery preparation and the surgery preparation are carried out by the surgeon manually without any assistance by computerised tools. E.G. the marking of the axis of the eye involves setting marks by a pen on the actual eye, which is a very tedious work for the surgeon. Moreover, the marks may become fuzzy or may disappear over time, which may negatively affect the performance and accuracy of the surgery.

During the actual surgery the surgeon only has the real-time image as he can see it through the surgical microscope, without any further indications which may assist him in performing the surgery.

It is therefore desirable to improve the whole process by providing the surgeon with a tool which can assist him in executing the aforementioned steps, in particular assisting him with the planning and also the execution of the surgery.

SUMMARY OF THE INVENTION

According to one embodiment there is provided image processing for computer-aided eye-surgery of an eye, comprising:
acquiring a reference image of the eye;
enriching said reference image by inserting additional context information which are helpful for a surgeon when performing the eye surgery;
registering said reference image with a real time image of the eye; and
overlaying the context information over the real time image of the eye based on a tracking of the eye movement such that the context information is displayed at the same position despite a movement of the eye.

In this way the surgeon is supported during surgery, but also during surgery planning by performing an image processing which assists the surgeon.

According to one embodiment further comprises:
determining a first coordinate system using a coordinate system determination algorithm based one or more features of the eye of the reference image;
determining the spatial location of the context information based on said coordinate system;
determining a second coordinate system in the real-time image taken during surgery using said coordinate system determination algorithm;
determining the location where to overlay said context information by determining the coordinate transformation from said first coordinate system to said second coordinate system.

In this way the absolute spatial location of the context information in the newly determined coordinate system of the reference image can be determined. This location can then later be used to accurately place the context information at the same location in the real-time image during surgery.

One embodiment the method comprises:
registering the reference image with an initial image of a real-time image sequence to obtain an initial coordinate transformation;
tracking the eye movement based on a comparison the further real-time images compared with the initial image of a real-time image sequence to obtain a second coordinate transformation, and obtaining a final coordinate transformation from said reference image to a real-time image of said real-time image sequence based on a combination of said first and said second coordinate transformations to enable a display of the context information in the real-time image based on said combined coordinate transformation; or
registering the reference image with the real-time images of a real-time image sequence to obtain coordinate transformation from said reference image to the real-time image of said realtime image sequence to enable a display of the context information in the real-time image based on said obtained coordinate transformation.

The first alternative uses an initial image of the real-time sequence and performed registration between the initial image and the reference image. This leads to a first coordinate transformation. Then there is performed tracking of the real-time images starting with the initial image to obtain a second coordinate transformation. Combining both transformation leads to the transformation which corresponds to the difference between reference image and a real-time image of the sequence.

Alternatively a registration could be directly performed between the reference image and the real-time images of the real-time image sequences, which may be computationally more expensive.

According to one embodiment said context information is one or more of the following:

diagnostic data which graphically represents properties or parameters of the eye which are useful for diagnostic purpose;

surgery planning data which indicate graphically one or more locations where or directions into which the surgeon should perform a certain surgical operation.

The surgery planning data which can be overlaid, significantly assists the surgeon to perform the right operation at the right place. Similarly the overlay of diagnostic information such as wavefront data or topometry data can be of great help during surgery.

According to one embodiment the location were the context information is overlaid on the real-time eye image is the same location as it was added to the reference image.

This is helpful if the surgeon e.g. wants to have the incision marks to be displayed at exactly the location where the incision is to be made.

According to one embodiment the context information overlay over the real-time image can be switched on and off by the surgeon.

This enables the surgeon to overlay and remove the context information as desired and as convenient.

According to one embodiment said context information is one or more of the following:

one or more incision marks for marking the location where in an incision has been made;

a cylinder axis for placing a toric intra-ocular lens;

one or more anchor areas for anchoring a device, e.g. for phakic intra-ocular lenses;

a pupil mark or a line of sight mark, e.g. for placing a phakic intra-ocular lens at the right position or for other purposes; or topometry data or wavefront data of the eye.

These are use cases where the operation principles of the invention can be applied in particular advantageous manner.

According to one embodiment there is provided an apparatus for image processing for computer-aided eye-surgery of an eye, comprising:

a module for acquiring a reference image of the eye;

a module for enriching said reference image by inserting additional context information which are helpful for a surgeon when performing the eye surgery;

a module for registering said reference image with a real time image of the eye; and a module for overlaying the context information over the real time image of the eye based on a tracking of the eye movement such that the context information is displayed at the same position despite a movement of the eye.

In this way an apparatus according to an embodiment of the invention can be implemented.

According to one embodiment the apparatus further comprises:

a module for determining a first coordinate system using a coordinate system determination algorithm based one or more features of the eye of the reference image;

a module for determining the spatial location of the context information based on said coordinate system;

a module for determining a second coordinate system in the real-time image taken during surgery using said coordinate system determination algorithm;

a module for determining the location where to overlay said context information by determining the coordinate transformation from said first coordinate system to said second coordinate system.

According to one embodiment said context information is one or more of the following:

diagnostic data which graphically represents properties or parameters of the eye which are useful for diagnostic purpose; or surgery planning data which indicate graphically one or more locations where or directions into which the surgeon should perform a certain surgical operation.

According to one embodiment the location were the context information is overlaid on the real-time eye image is the same location as it was added to the reference image.

According to one embodiment the context information overlay over the real-time image can be switched on and off by the surgeon.

According to one embodiment said context information is one or more of the following:

one or more incision marks for marking the location where in an incision has been made;

a cylinder axis for placing a toric intra-ocular lens;

one or more anchor areas for anchoring a device, e.g. for phakic intra-ocular lenses;

a pupil mark or a line of sight mark, e.g. for placing a phakic intra-ocular lens at the right position; or topometry data or wavefront data of the eye.

According to one embodiment there is provided a computer program comprising computer program code which when being executed on a computer enables said computer to carry out a method according to one of the embodiments of the invention.

DESCRIPTION OF THE DRAWINGS

FIG. 4 schematically illustrates the overlay of context information in an apparatus according to an embodiment of the invention.

FIG. 5 schematically illustrates the overlay of context information in an apparatus according to a further embodiment of the invention.

FIG. 6 schematically illustrates the overlay of context information in an apparatus according to a further embodiment of the invention.

FIG. 7 schematically illustrates the overlay of context information in an apparatus according to a further embodiment of the invention.

FIG. 8 schematically illustrates the overlay of context information in an apparatus according to a further embodiment of the invention, FIG. 9 schematically illustrates the diagnostic image, surgery planning and overlay of context information in an apparatus according to a further embodiment of the invention.

FIG. 10 schematically illustrates the surgery planning according to an embodiment of the invention.

DETAILED DESCRIPTION

According to one embodiment there is provided an apparatus which achieves an improvement of the intraocular lens surgery process by linking diagnostic and pre-surgery planning results of a patient's eye directly with the patient's eye under the surgeon's microscope.

This leads to significant advantages compared to the conventional "manual" process. Some advantages are listed below.

Speeding up and simplification of the full process: No more time consuming ink markers and stamp tools are needed in the IOL process, especially for toric IOLs.

Accuracy of the process: Error prone marker and print-out techniques are avoided.

Safety of the process: Due to the consistent coordinate between diagnostic and IOL surgery as well as the thorough planning of the surgeon before surgery, the number of outliers due to process mistakes can be reduced.

As already explained above, the conventional IOL surgery process starts with a diagnosis of the eye to be treated. Usually the geometry of an eye (length, chamber depth, lens thickness, etc.) is determined using an IOL Master (a medical device, manufactured e.g. by Zeiss). Additionally often the topometry and the refraction of an eye is determined in advance. This diagnostic data is used to define the IOL type and IOL geometry that should be implanted.

Figure 1:
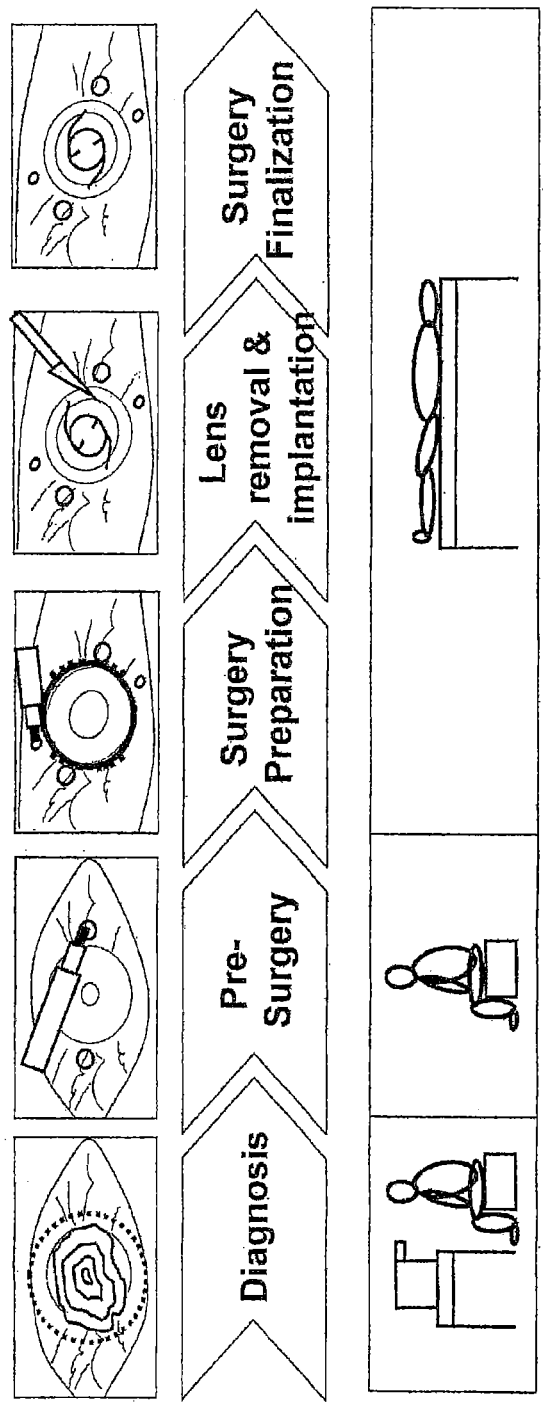
FIG. 1 schematically illustrates a conventional IOL surgery process.
Figure 2:
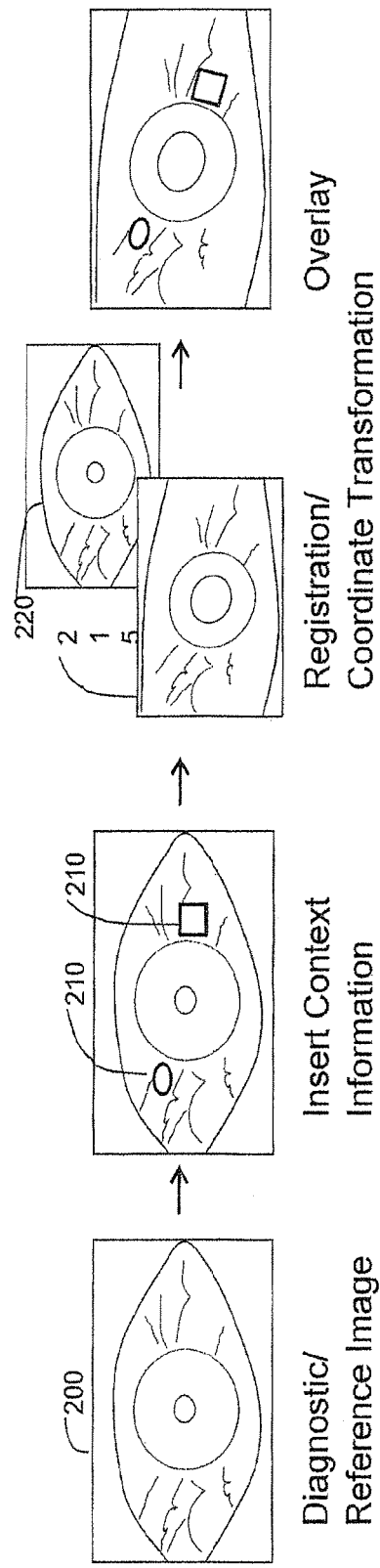
FIG. 2 schematically illustrates the operation principles of an apparatus according to an embodiment of the invention.

In the following there will be explained an embodiment of the invention which assists the surgeon with the process of performing IOL surgery. Referring to FIG. 2 the operation of such a device which can assist the surgeon will be explained. At first there is acquired an image 200 of the eye which can be used for diagnosis and especially is then used as a reference image in the further procedure of the operation. Using the thus acquired reference image, the surgeon by means of some graphical manipulation tool or image processing tool can insert context information 210 into the reference image or add context information to the reference image, such as e.g. marking one or more locations or regions in the image. The result is that the reference image is "enriched" by some context information which later can be useful or helpful for the surgeon when performing the actual surgery.

Moreover, by inserting some context information there is defined a relationship between the coordinate system of the reference image and the coordinates where the context information is located. In other words, by marking e.g. a point or a region in the reference image the coordinates of such a point or a region are fixed with respect to the coordinate system of the reference image (or with respect to a certain fixpoint in the reference image). This means that by adding the context information there is established a location definition which defines the position in the reference image at which the context information is located (i.e. the coordinates of the context information in the coordinate system of the reference image).

As a result of the insertion or addition of context information, the reference image contains this additional information (context information) and may be regarded as having two components, the first component being the actual reference image which has been acquired and a second component being the additional context information (with its location in or with respect to the reference image). In FIG. 2 the schematically illustrated context information 210 can for example be markers which show the surgeon where to make incisions during the surgery.

According to one embodiment the context information is stored and treated separately from the reference image, e.g. as a separate file or dataset. This makes it possible to maintain the original reference image and the context information separately, e.g. if (as will be described later in more detail) only the context information is to be overlaid onto the real-time image during surgery. Also if stored and treated separately from the reference image (or the "diagnostic image) the context information includes information about the location of the context information in the reference image, so that at a later time it will always be possible to "insert" the context information at a later stage in the reference image or in the real-time image during surgery. The latter may then involve additional coordinate transformation based on registration and tracking, as will be explained later in more detail.

Before the definition of the context information the operation may include the definition of the coordinate system in the reference image. This means that there is defined a coordinate system in such a manner that in another image, which is acquired later, the same coordinate system can be determined again with the origin of the coordinate system lying at the same location in the eye and having the same orientation as in case of the coordinate system determined for the reference image. For this purpose there may be carried out a coordinate system determination which uses fixed points or features of the eye which do not change (or do not significantly change) over time, such as the limbus or other eye features like scleral blood vessels. By referring to these features an origin of a coordinate system may be defined or determined, either manually or automatically, however, in any case in such a way that the coordinate system can again be determined (or found) at the same position in the eye at a later time. From a comparison of the location of the coordinate system in the reference image and the same coordinate system in the real-time image (or an initial image of a real-time image sequence) one can then determine a coordinate transformation which has to be applied to shift one coordinate system such that it coincides with the other one, as will be explained later in more detail.

After the definition of the context information (and its location with respect to the coordinate system of the reference image) the operation of the apparatus then further proceeds by performing a registration of the diagnostic or reference image 220 with the actual real-time image 215 as taken by a camera from the patient "live".

The registration process has the effect that there is determined the coordinate transformation which is necessary to "shift" the reference image such that it matches with the actual live image 215 (or a selected actual live image at a certain time) of the patient. Using the registration (and the coordinate transformation parameters resulting there from) there can be performed then a coordinate transformation of the "context information" which have been added to the reference image so that in the next operation step there can be performed an overlay of the context information over the actual real time image of the patient's eye. By using an eye tracking mechanism according to the prior art this overlaid image which contains context information can be "tracked" with the movement of the eye in real time, so that the surgeon then always has on his monitor a real time image of the eye with additional context information overlaid which can assist him with performing (or planning the surgery).

Therefore, at first there is performed a registration as an initial shift of the reference coordinate system by a coordinate transformation $z1$ such that it matches with a selected real-time image of the eye at a certain time t, and then for times later than t there is determined a further coordinate transformation $z2$ at each time, and this second transformation $z2$ compensates for the eye movement at times later than t. The two coordinate transformations $z1$ and $z2$ together then enable a movement compensation of the eye and allow the context information to be overlaid onto the real-time eye image at a fixed location with respect to the eye, despite the eye's movement.

Figure 3:
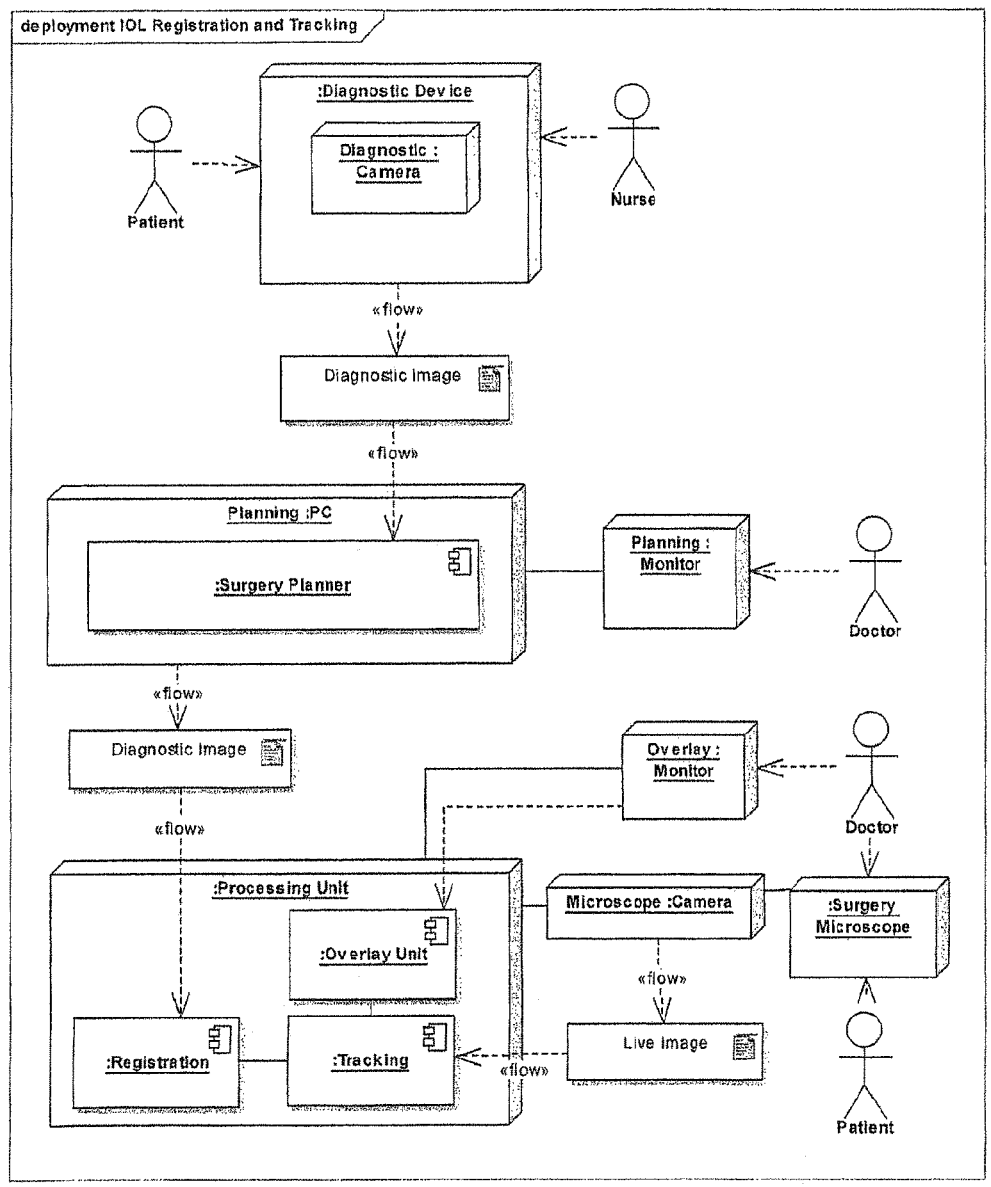
FIG. 3 schematically illustrates an apparatus according to an embodiment of the invention.

An apparatus for performing the operations as explained before in connection with FIG. 2 is schematically illustrated in FIG. 3. A diagnostic device (which may be operated by a nurse) includes a diagnostic camera (or reference image camera) which then acquires the diagnostic image or reference image.

The images are stored and processed in a computer (such as a PC) and the computer then performs a processing which allows the user to perform graphical manipulations or graphical image processing in order to enrich the acquired reference image with context information, in other words to "add" context information to the reference image or to "define" the context information. The context information may be any information which assists the surgeon while performing the surgery. In particular this may involve marks which are useful for planning (and then performing) the surgery or it may also involve diagnostic information.

For adding the context information there is provided a "planning monitor" which may comprise a screen or a touch screen on which the physician then can insert (or add or define) context information by a graphical manipulation tool, e.g. by selecting one or more positions or regions in the reference image which should be marked, so that there results then a reference image enriched by context information. The surgeon may e.g. just select points or regions, and in this way he may define locations in the eye where the context information is to be displayed.

The result of the "surgery planner", which actually consists of a computer which executes a suitable graphical processing to produce the enhanced reference image, is then the reference image or diagnostic image which is enriched by context information. In another embodiment it is a separate dataset or file which includes the context information, the context information including a definition of one or more positions in the eye where the context information is located. The context information may further in addition to its location may include the actual context information which may just be a single bit indicating the corresponding position as selected, or it may include more detailed information such as the colour or the style (dashed line or non-dashed line, etc.) in which it should be displayed.

The thus enriched reference image then is inputted into a processing unit (which may again be a PC, according to one embodiment even the PC which also forms the surgery planner) which performs registration of the reference image with the real time image of the eye (live image) and then also performs a tracking of the live image. For that purpose there is provided a surgery microscope for which a camera acquires an image of the patient's eye. Based thereupon and based further on the enriched reference image the registration and tracking is performed by the processing unit.

In one embodiment the registration may be performed based on the non-enriched reference image, assuming that the context information is stored in a separate file and is then only used later after the registration using the "pure" reference image as been performed.

Then there is provided an additional component, the "overlay unit. This overlay unit may also be implemented by a PC or by a module of the processing unit which performs the registration and tracking. The overlay unit performs operation of "overlaying" the context information on the live image of the patient's eye. For that purpose the overlay unit makes reference to the coordinate transformation data which has been obtained by the registration process, and which represents the positional shift which has to be performed so that the reference image matches with the live image. This coordinate transformation then is applied to the context information which can then be displayed in the real-time live image of the eye. This results in an overlay where the real-time image of the eye has overlaid the additional context information which has been added to the reference image during the step of adding context information. By applying an eye tracking mechanism (which in principle is known in the art) the overlay can follow the movement of the eye so that the context information is overlaid always at the same position at which it has been added during the planning phase, despite the movement of the eye.

The result then is that on the screen connected to the computer (which is indicated in FIG. 3 as "overlay monitor" the physician can see the live image enriched by the context information which are overlaid on the live image and which follows the movement of the eye so that it always is displayed at the same position of the live image, which in one embodiment is actually the position at which it has been added to the reference image.

In the following there will be explained in somewhat more detail some further embodiments which show how the standard intraocular lens surgery workflow can be significantly improved using registration and tracking for IOL surgery.

According to one embodiment which will be described in the following there is provided a tool for incision planning for IOL surgery.

For every IOL surgery the doctor has to place multiple cuts (=incisions) in the eye to bring in surgery tools under the cornea for e.g., removing the existing lens, inducting the folded IOL, positioning the IOL, inducing and removing temporary fluids. Incisions are placed near the limbus border in the scleral area or even in the cornea. Due to the physical behaviour of the cornea and depending on the position of the incision, astigmatism can be induced to the cornea of up to several diopters. This well known effect is usually used to compensate existing astigmatisms by choosing the right incision position. Inaccurate placement of incisions may lead to additional astigmatism or less compensated astigmatism and therefore a decreased visual outcome for the patient. Incision planning is based on several methods, all mainly based on the topometry of the cornea.

Using registration and tracking for IOL surgery, an intermediate surgery planning step can be introduced, where a doctor is planning—after receiving the diagnostic data and before the surgery—the best fitting incisions for the patient. The incisions can be tagged and labelled as visual context information on the diagnostic image. Using registration for IOL surgery the eye coordinate system of the diagnostic image is registered to the eye coordinate system at the surgery. Using tracking for IOL surgery, the eye coordinate system during surgery is consistently matched with the diagnostic eye coordinate system. This way the doctor is able to overlay the visual context information added in the surgery planning step on top of the current surgery microscope image.

It should be noted here that the reference image where the context information is added to may be a "pure" image of the eye or may be a diagnostic image which may include additional information such as topometry information.

FIG. 4 schematically illustrates an eye image where there are overlaid incision markers which are regions which have been marked on the reference or diagnostic image during the planning phase and which are now overlaid on the real-time live image of the eye during surgery.

What can be seen in FIG. 4 is that not only the incision marks are displayed, but also angular marks from 0° to 180° for the upper half and from 0° to 180° for the lower half. These angular marks have e.g. been fitted to the limbus during the planning of the surgery, and the 0° line has been chosen to coincide with the x-axis of the coordinate system in the diagnostic image. The coordinate system in the diagnostic image has been chosen such that its origin e.g. coincides with the center of the limbus and its x-axis is parallel with the x-direction of the image.

It can be seen from FIG. 4 that due to the registration and tracking on the right-hand side the 0° line of the angular indication is inclined compared to the x-axis of the coordinate system (the 0° line in the coordinate system of the real-time image which again is chosen to be horizontal in the image). This is an indication that the eye has rotated compared to the position it had when the context information was defined (when the incision marks were added). The angular indication marks (from 0° to 180°) therefore indicate how much the real-time image is inclined (or rotated) compared to the diagnostic or reference image at which the incision marks have been marked during the planning phase. By registration and/or tracking between the reference image and the real-time image there is obtained the coordinate transformation which transforms the diagnostic image into the real-time image, and this coordinate transformation is then applied to the context information (in FIG. 4 the incision marks and also the angular indications) so that the context information is then actually displayed on the correct location in the real-time image. In other words, the incision marks displayed in the real-time image (on the right-hand-side of FIG. 4) are displayed at exactly the location where the surgeon has to apply the incisions, despite the movement of the eye. This is due to the coordinate transformation which is applied to the context information before it is overlaid onto the real-time image.

In this way the context information (the incision marks shown on the right-hand side of FIG. 4) are displayed on the correct location, despite the eye movement, and therefore the context information (here: the incision marks) can assist the surgeon performing the surgery in real-time.

According to a further embodiment which will be described in the following there is provided an apparatus for assisting the surgeon with the angular placement of toric IOLs.

For dedicated surgeries IOLs with additional cylinder compensating optics are used, so called "toric IOLs". During surgery the surgeon has to ensure that the cylinder of the toric IOL matches the cylinder of the cornea. In the conventional surgery process this is ensured using multiple manual steps based on ink markers and stamps to re-identify the 0° line from the diagnostic to the surgery. There are several assumptions in this manual process, that are prone to error: (1) the patient's eye is not changing rotation after sitting in front of different devices (2) ink markers are stable from diagnosis to surgery (3) stamps can be used accurately during surgery, to label the cylinder axis. All three assumptions must be seen to be wrong in practice. There can be errors introduced easily from 2° to 5° by each manual step based on these assumptions. Knowing that a 10° off toric IOL looses its capability of compensating a cylinder of the cornea shows how significant these errors can be. This might be a major reason why so far toric IOLs are currently used at a rate below 2% of all IOL surgeries, even if the theoretical outcome should be better compared to standard spherical IOL.

By using registration and tracking for toric IOL surgery, however, the intermediate surgery planning step can be used to identify the best cylinder axis aligning the toric IOL for the patient's eye. The cylinder axis can be tagged and labelled as visual context information on the diagnostic image by selecting the corresponding location or locations in the diagnostic or reference image. For the addition of the context information there is in one embodiment provided a graphical user interface which enables the surgeon to select or input the context information, e.g. through the mouse or the keyboard, our by means of a touch screen.

Using registration for IOL surgery the eye coordinate system of the diagnostic image is registered to eye coordinate system at the surgery. Using tracking for IOL surgery, the eye coordinate system during surgery is consistently matched with the diagnostic eye coordinate system. In other words, there is determined the coordinate transformation which has to be applied to shift the reference image coordinate system such that it coincides with the corresponding coordinate system in the real-time image. This way the surgeon is able to overlay the visual context information added in the surgery planning step on top of the current surgery microscope image. All manual, ink based steps for transforming the coordinate system become obsolete in this embodiment, and the usage of toric IOLs therefore becomes much easier for the surgeon.

FIG. 5 schematically illustrates an eye image where there is overlaid the 0° line of the diagnostic image (the dotted line). Also shown is the 0° line of the actual live image (the full x-axis) and the orientation for the toric lens (the dashed line). From comparison with the reference coordinate system (a comparison between the x-axis in the real-time image and the dotted line which is the 0° line in the diagnostic image) the surgeon can identify how much the real-time image has been inclined compared to the diagnostic image. From the dashed line he can identify the direction along which the toric lens has to be aligned, because similarly to the previous embodiment the dashed line due to the application of a coordinate transformation which is obtained from registration and/or tracking between the reference image and the real-time image the dashed line is displayed on a location which compensates for a movement of the real-time image compared with the reference image.

The reason that the two lines (the diagnostic 0° line and the 0° line of the real-time image) do not match each other in this embodiment is that there has been some movement of the eye from the reference image to he real-time image during surgery. This is reflected by the inclination between the 0° line of the reference image (shown as dotted line) and the x-axis of the real-time image (shown as full line and as x-axis of the coordinate system in the real-time image). If in the real-time image the eye would not have moved at all and would be located at exactly the same location and exactly aligned in the same way as it was when the reference image was taken, then the dotted line (0° line of the reference image) and the x-axis of the real-time image would coincide. However, due to the movement of the eye the coordinate system which was initially defined in the reference image (based on one or more features or landmarks of the eye) is now shifted and possibly also rotated, and therefore diagnostic 0° line and the 0° line of the real-time image typically do not coincide anymore, as can be seen from FIG. 5.

In FIG. 5 there is shown the 0° line which can be automatically determined in the reference image and also in the real-time image, e.g. by using the limbus and other eye features. The limbus may e.g. be fitted by a circle and then the center may be used as the origin of the coordinate system. Any other feature (e.g. a blood vessel may be used as a reference to determine the direction of the x- and y-axis, where the actual direction of these axis is not so important as long as the determination algorithm for the coordinate system is unambiguously determining the location of the coordinate system so that the coordinate system in the reference image and the real-time image is located at the same position in the eye. Once the coordinate system has been determined, the x-axis of the coordinate system may be highlighted as the 0° axis (as shown in FIG. 5 as dotted line), and additionally there can then be displayed overlaid the alignment-axis (shown as dashed line in FIG. 5) along which the toric IOL should be aligned. This latter axis has been determined by the surgeon using a graphical user interface (e.g. by the mouse) during the surgery planning phase when he added the context data to the reference image. The 0° line (the dotted line) and the alignment axis (the dashed line) are displayed in the real-time image based on a coordinate transformation which is obtained from registration and/or tracking between the reference image (where the ° line and the alignment axis have been defined) and the real-time image. By re-locating the coordinate system of the reference image in the real-time image one can obtain the coordinate transformation to make the two coordinate systems coincide, and this coordinate transformation is applied to the context data (the 0° line (the dotted line) and the alignment axis (the dashed line)) so that they are displayed at the same location in the real-time image at which they have been defined in the reference image. Therefore the surgeon can use the alignment axis shown in FIG. 5 for aligning the toric lens.

According to a further embodiment which will be described in the following there is provided an apparatus for assisting the surgeon with the lateral and angular placement of phakic IOLs.

Phakic IOLs are placed in front of the iris of a patient's eye and are anchored with dedicated fixation elements or haptics to the iris. The existing human eye lens remains in the eye to work together with the newly inserted Phakic IOLs to allow accommodation for near and far vision. Because there are multifocal, toric or multifocal-toric Phakic IOLs available, the lateral and toric placement of this Phakic IOLs is of special interest.

In theory the position of the photopic pupil (small) and scotopic pupil (large) as well as the line of sight might be beneficial at surgery time to place the center of the Phakic IOL. This way an accurate compensation of the eye optics using a Phakic IOL—especially a multifocal Phakic IOL—could be achieved. But in practice so far Phakic IOLs are positioned without this information. Conventionally visual or mental defects with the lens are identified after the surgery and corrected by making a re-surgery.

However, by using registration and tracking for Phakic IOL surgery, the intermediate surgery planning step can be used to identify the exact position of the Phakic IOL for the patient's eye taking into account translations and rotation of the Phakic IOL, and taking into account the limbus position, the photopic pupil, the scotopic pupil, and the line of sight. Knowing the final position of the Phakic IOL the anchor areas for the haptics can be planned as well.

All of the above-mentioned information can be tagged and labelled as visual context information on the diagnostic image. The photopic pupil and the scotopic pupil may e.g. be measured in the diagnostic image. Using registration for IOL surgery the eye coordinate system of the diagnostic image is registered to eye coordinate system at the surgery, and then the context information such as photopic and scotopic pupil can be overlaid on the real-time image using the coordinate transformation determined by the registration. Using tracking for IOL surgery, the eye coordinate system during surgery is consistently matched with the diagnostic eye coordinate system. This way the doctor is able to overlay the visual context information added in the surgery planning step on top of the current surgery microscope image.

FIG. 6 is a figure where as a context information the pupil as determined for example as an average of the photopic and scotopic pupil during the diagnostic/planning phase is indicated as overlay in the real-time image. This information helps the surgeon during the phakic IOL surgery. Depending on the individual diagnostic of the doctor, a standard pupil can be derived e.g. from the photopic and scotopic pupil and linked to the diagnostic image in the surgery planning step and can be overlaid on the real-time image. This is shown in FIG. 6 as dotted circle, in addition to anchor areas for anchoring the IOL have been defined using the reference image are displayed in the real-time image as shown in FIG. 6.

FIG. 7 is a figure where as a context information the line of sight (which also may have been determined during the planning or diagnostic phase) is overlaid on the real-time image.

The same planning, registration and tracking technique can be applied for related surgery areas, where positioning and rotation of implants is significant for clinical outcome. Examples would be corneal inlays or corneal onlays.

According to a further embodiment which will be described in the following there is provided an apparatus for assisting the surgeon by overlaying diagnostic data such as corneal topometry data or the wavefront data.

In this embodiment it is assumed that registration between diagnostic and surgery is based on 6D registration and tracking during surgery is based on 6D tracking. An apparatus which is capable of performing such a 6-dimensional registration and tracking is e.g. disclosed in DE 10 2006002 001 A1. With such a system even more sophisticates data can be visualised during surgery as will become apparent in the following.

Conventionally topometry data is usually determined from a single image or single perspective of a diagnostic device. One assumption is that the patient is fixating to the center of the diagnostic device, which is in practice not always the case. Using 6D registration from diagnostic to surgery, however, the fixation of the patient is no longer relevant. Using 6D registration the former position of the eye in all six degrees of freedom can be determined and the topometry data of the cornea can be visualised during surgery as an online re-computed topometry of the cornea depending on the 6D position of the eye under the microscope.

In this embodiment there is determined the six-dimensional location of the eye, and then as additional context information the corneal topometry or wavefront data is acquired. This data which has been acquired during the diagnostic step in its 6-dimensional spatial relationship to the 6-dimensional eye image can then be stored and after registration and by using tracking it can be overlaid over the real-time image of the eye during surgery. This is done by re-computing the position of the 6-dimensional diagnostic information (wavefront or topometry data) based on the coordinate transformation obtained form registration and tracking. Then this diagnostic data (wavefront or topometry data) can be displayed by overlaying it onto the real-time image of the eye during surgery.

This is highly advantageous for the surgeon and helps him with performing the surgery. FIG. 8 exemplarily illustrates the overlay of such data as topometry data or wavefront data.

Compared to other approaches where it is tried to make a real-time wavefront measurement during surgery (such as described in US 2005/0241653 A1), this approach has significant advantages. One main advantage of this method is that the cornea is not measured during surgery on a physically manipulated eye, but during diagnosis on a relaxed eye. This way the visualised information during surgery is independent from the surgery conditions of the eye, and the overlaid information is the "real" diagnostic information without the distorting effect which is caused by the physical manipulation of the eye during surgery.

In the following there will be described in connection with FIG. 9 a further embodiment and how it three different process phases, namely diagnostic, surgery planning and surgery.

On the diagnostic side the doctor uses a diagnostic device (e.g. a topometer or IOL-master) to determine the parameters required for later IOL surgery. The device must be capable to acquire images of the eye with sufficient pixel resolution and visible illumination (e.g., white or green) to allow registration and tracking for IOL surgery. This "Diagnostic Image" will be used as a reference image defining the original coordinate system for the diagnostic data and all following process steps. FIG. 9 the upper part schematically illustrates such a diagnostic image or reference image. The diagnostic step may further involve the acquisition of topometry data or wavefront data, as was explained before.

The surgery planning step is an intermediate step between diagnosis and surgery that allows the doctor to plan its future actions in the surgery. On the Diagnostic Image the limbus and eye features outside the limbus are measured, to define the original coordinate system. Different type of context information (e.g. incisions, cylinder axis, line of sight, etc.) can be linked to this original coordinate system by adding, overlaying, manipulating and enriching visual elements onto the diagnostic image using the Surgery Planner software which in one embodiment is a graphical user interface allowing the user to define locations or regions in the diagnostic image. The software may include a helping function which supports the doctor in finding the right incisions, cylinder axis or other relevant parameters, by executing some algorithms which are able to calculate relevant positions for surgery planning using existing literature data.

Figure 9:
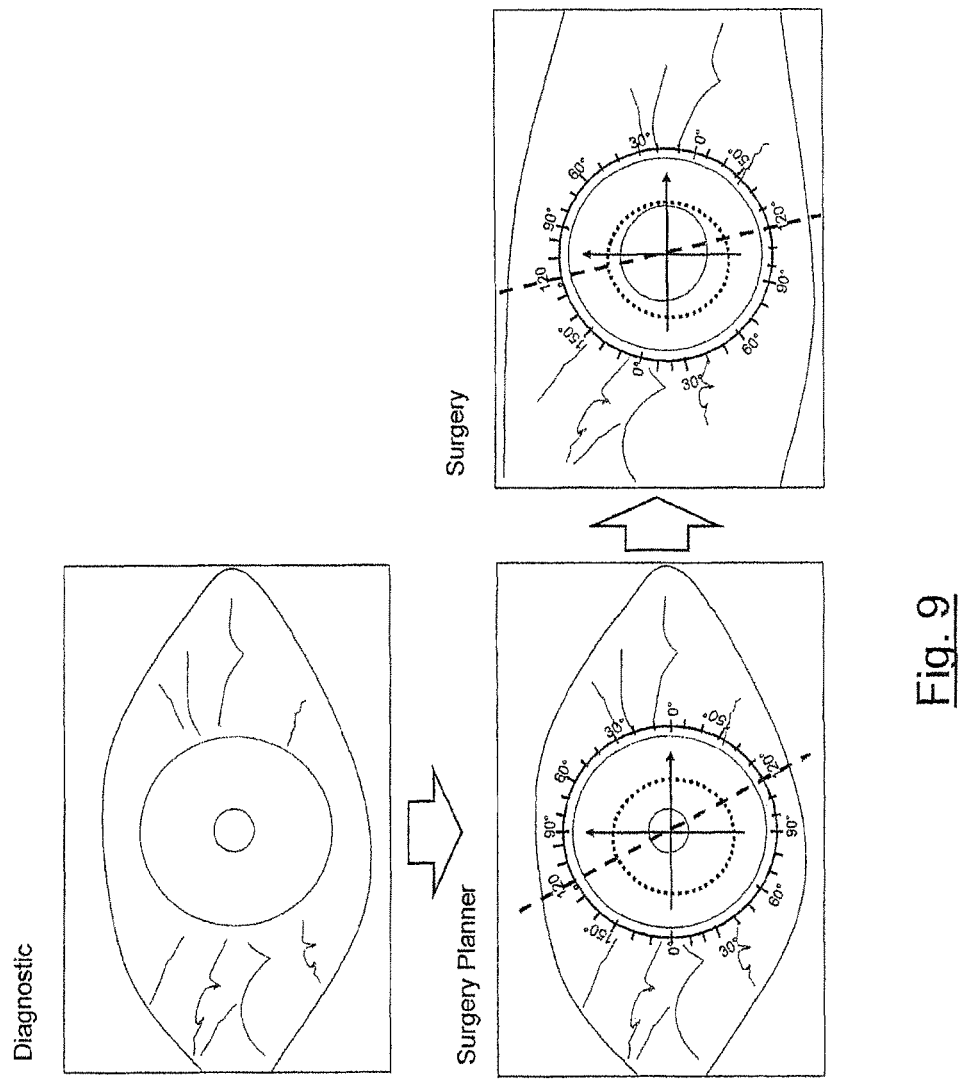

In the embodiment shown in FIG. 9, the lower left part illustrates exemplarily the planning with the insertion (or definition) of a standard pupil (the dotted circle) and the definition of a cylinder axis (the dashed line, e.g. for aligning toric lenses).

The doctor can do the planning step independent of the presence of the patient and with no time pressure e.g. due to fading ink markers. Multiple patient sessions can be planned sequentially due to the fixed coordinate system which can be recalculated and reused in later sessions, as it is also then later used during surgery.

The output data of the Surgery Planner software (Planning Content) of a patient may be transferred to the surgery environment using network or memory stick devices. According to another embodiment the planning step is performed at the same computer as the surgery registration and tracking, then no such transfer is necessary.

In the surgery environment the registration and tracking processing unit acquire and process online eye images from the microscope camera (surgery mages). A (touch screen) monitor near the surgeons chair or a monitor in the microscope then displays the surgery images online (real-time). In one embodiment interactions with the processing unit which carries out the tracking and overlay processing are possible via a touch screen monitor or a foot paddle, e.g. to switch the overlay information on or off. The Planning Content (context information) of the current patient is be loaded to the processing unit that is linked to the microscope camera, and through registration and tracking it can be overlaid on the real-time image during surgery.

At the beginning of the surgery after preparation of the patient's eye the doctor activates the registration from the Diagnostic Image to the Surgery Image to determine the absolute coordinate transformation from diagnostic to surgery (Diagnostic Transformation). The selected Surgery Image, where the registration to the Diagnostic Image is successful, will be stored as Surgery Reference image.

During the surgery, the doctor can activate the overlay functionality every time he or she wants to visualize the Planning Content (the context information). This is achieved by tracking the eye under surgery conditions, where for each tracking period P the Diagnostic Transformation (which is the transformation from the diagnostic image to the surgery reference image) and the coordinate transformation from the current Surgery Image to the first Surgery Image of P is added. In this way the context information is displayed always at the same location in the real-time image of the eye, despite the movement of the eye.

In the example of FIG. 9 the overlay is shown on the lower right-hand side. From the displacement of the 0° line with the 0° line of the real-time image one can see that in this example the eye does not completely match the orientation of the eye at the diagnostic or reference phase. There is some rotational displacement between the diagnostic image and the real-time image which is visualized by the 0° line as indicated by the angular indications is inclined compared to the x-axis of the image itself.

FIG. 10 shows in somewhat more detail the actual surgery planning step. At first (left-hand-side of FIG. 10) there is determined the coordinate system in the reference image, e.g. such that the origin matches with the center of the limbus and that the x-axis is parallel to the x-direction of the image itself. Then there is calculated an angular indication where a circle fitted to the limbus id divided in an upper half marked with angles from 0° to 180° and a lower half marked with angles from 0° to 180°. Based on this diagnostic reference image then, as shown in the right-hand side of FIG. 10, the context data, here exemplarily an axis (dashed line) and a standard pupil (dotted circle) are added. Other context information such as incision marks could be added in a similar manner.

For context information like incision markers or the alignment axis the whole operation can be performed using only 2-dimensional images. However, if such information as topometry data or wavefront data are to be used as context information there is preferably used a 6-dimensional registration and tracking process, as explained before.

The embodiments described before lead to significant advantages of the prior art, some of which are listed below. Summarizing there are the following outstanding advantages of this invention:

Speeding up and simplification of the IOL surgery process: No more time consuming ink markers and stamp tools are needed in the IOL process, especially for toric IOLs.

Accuracy of the process: Error prone marker and print-out techniques are avoided.

Safety of process: Less outliers due to automated link between diagnostic and surgery Diagnostic data of relaxed eye is used for surgery planning and surgery (and not distorted eye data obtained during surgery)

The whole apparatus can be relatively easily integrated into existing surgery microscopes by adding a camera which takes digital images and a processing unit which allows the acquisition of the diagnostic or reference image, the addition of context information, and the use of the context information for overlaying it onto the real-time image based on registration and tracking.

It will be understood by the skilled person that the embodiments described hereinbefore may be implemented by hardware, by software, or by a combination of software and hardware. The modules and functions described in connection with embodiments of the invention may be as a whole or in part implemented by microprocessors or computers which are suitably programmed such as to act in accordance with the methods explained in connection with embodiments of the invention.

According to an embodiment of the invention there is provided a computer program, either stored in a data carrier or in some other way embodied by some physical means such as a recording medium or a transmission link which when being executed on a computer enables the computer to operate in accordance with the embodiments of the invention described hereinbefore.

Having described and illustrated the principles of the invention in representative embodiments thereof, it should be apparent that the invention may be modified in arrangement and detail without departing from such principles. We claim all modifications and variation coming within the spirit and scope of the following claims.

The invention claimed is:

1. A method for image processing for computer-aided eye-surgery, said method comprising:
   acquiring a reference image of the eye;
   enriching said reference image by inserting additional context information helpful for a surgeon when performing the eye surgery;
   registering said reference image with a real-time image of the eye, wherein registering the reference image with the real-time image includes determining an angular displacement between the real-time image and the reference image; and
   overlaying the context information and a visual representation of the angular displacement over the real-time image of the eye based on a tracking of the eye movement such that the context information is displayed at the same relative position on the real-time image as the enriched reference image despite a movement of the eye and such that the visual representation of the angular displacement indicates an amount of angular displacement of the real-time image relative to the reference image.

2. The method of claim 1, further comprising:
   determining a first coordinate system using a coordinate system determination algorithm based one or more features of the eye of the reference image;
   determining the spatial location of the context information based on said first coordinate system;
   determining a second coordinate system in the real-time image taken during surgery using said coordinate system determination algorithm; and
   determining the location where to overlay said context information by determining the coordinate transformation from said first coordinate system to said second coordinate system.

3. The method of claim 1, further comprising:
   registering the reference image with an initial image of a real-time image sequence to obtain a first coordinate transformation;
   tracking the eye movement based on a comparison of further real-time images compared with the initial image of a real-time image sequence to obtain a second coordinate transformation, and obtaining a final coordinate transformation from said reference image to a real-time image of said real-time image sequence based on a combination of said first and said second coordinate transformations to enable a display of the context information in the real-time image based on said combined coordinate transformation; or
   registering the reference image with the real-time images of a real-time image sequence to obtain coordinate transformation from said reference image to the real-time image of said real-time image sequence to enable a display of the context information in the real-time image based on said obtained coordinate transformation.

4. The method of claim 1, wherein said context information is one or more of the following:
   diagnostic data which graphically represents properties or parameters of the eye which are useful for diagnostic purpose;
   surgery planning data which indicate graphically one or more locations where or directions into which the surgeon should perform a certain surgical operation; or
   implant placement data which indicate graphically one or more locations where and or orientation of or directions into which an implant shall be placed onto or into the eye.

5. The method of claim 1,
   wherein the context information overlaid over the real-time image can be switched on and off by the surgeon.

6. The method claim 1, wherein said context information is one or more of the following:
   one or more incision marks for marking the location of an incision;
   a cylinder axis for placing a toric intra-ocular lens;
   one or more anchor areas for anchoring a device;
   a pupil mark or a line of sight mark;
   topometry data or wavefront data of the eye; or
   the position of corneal inlays or corneal onlays.

7. The method of claim 1, wherein the image processing is performed by a computer program comprising computer program code which when being executed on a computer enables said computer to carry out the method according to claim 1.

8. An apparatus for image processing for computer-aided eye-surgery, comprising logic circuitry configured to:
   acquire a reference image of the eye;
   enrich said reference image by inserting additional context information helpful for a surgeon when performing the eye surgery;
   register said reference image with a real-time image of the eye, wherein registering the reference image with the real-time image includes determining an angular displacement between the real-time image and the reference image; and
   overlay the context information and a visual representation of the angular displacement over the real-time image of the eye based on a tracking of the eye movement such that the context information is displayed at the same relative position on the real-time image as the enriched reference image despite a movement of the eye and such that the visual representation of the angular displacement indicates an amount of angular displacement of the real-time image relative to the reference image.

9. The apparatus of claim 8, wherein the logic circuitry is further configured to:
   determine a first coordinate system using a coordinate system determination algorithm based one or more features of the eye of the reference image;
   determine the spatial location of the context information based on said coordinate system;
   determine a second coordinate system in the real-time image taken during surgery using said coordinate system determination algorithm; and determine the location to overlay said context information by determining the coordinate transformation from said first coordinate system to said second coordinate system.

10. The apparatus of claim 8, wherein the logic circuitry is further configured to:
register the reference image with an initial image of a real-time image sequence to obtain a first coordinate transformation, and
track the eye movement based on a comparison of further real-time images compared with the initial image of a real-time image sequence to obtain a second coordinate transformation, and obtaining a final coordinate transformation from said reference image to a real-time image of said real-time image sequence based on a combination of said first and said second coordinate transformations to enable a display of the context information in the real-time image based on said combined coordinate transformation; or
register the reference image with the real-time images of a real-time image sequence to obtain coordinate transformation from said reference image to the real-time image of said real-time image sequence to enable a display of the context information in the real-time image based on said obtained coordinate transformation.

11. The apparatus of claim 8, wherein said context information is one or more of the following:
diagnostic data which graphically represents properties or parameters of the eye which are useful for diagnostic purpose;
surgery planning data which indicate graphically one or more locations where or directions for performing a certain surgical operation; or
implant placement data which indicate graphically one or more locations where and or orientation of or directions into which an implant shall be placed onto or into the eye.

12. The apparatus of claim 8, wherein the context information overlay over the real-time image is configured to be switched on and off.

13. The apparatus of claim 8, wherein said context information is one or more of the following:
one or more incision marks for marking the location where in an incision has been made;
a cylinder axis for placing a toric intra-ocular lens;
one or more anchor areas for anchoring a device;
a pupil mark or a line of sight mark for placing a phakic intra-ocular lens at the right position;
topometry data or wavefront data of the eye; or
the position of corneal inlays or corneal onlays.

* * * * *